United States Patent [19]

Riley

[11] 4,446,152

[45] May 1, 1984

[54] METHOD OF TREATING CONGESTIVE HEART FAILURE

[75] Inventor: Richard L. Riley, North Wales, Pa.

[73] Assignee: William H. Rorer, Inc., Fort Washington, Pa.

[21] Appl. No.: 277,148

[22] Filed: Jun. 25, 1981

[51] Int. Cl.³ ............................................. A61K 31/17
[52] U.S. Cl. .................................. 424/322; 424/304; 424/315
[58] Field of Search ........................ 424/322, 304, 315

[56] References Cited

U.S. PATENT DOCUMENTS 4,088,785 5/1978 Diamond et al. .................. 424/322

Primary Examiner—Leonard Schenkman
Attorney, Agent, or Firm—Austin R. Miller

[57] ABSTRACT

This invention relates to a composition and method of treating congestive heart failure in warm blooded animals, employing substituted phenylamidinourea compounds as the active agents.

6 Claims, No Drawings

METHOD OF TREATING CONGESTIVE HEART FAILURE

SUMMARY OF THE INVENTION

This invention relates to a method of treating congestive heart failure in warm blooded animals, employing substituted amidinourea compounds as the active agent.

BACKGROUND OF THE INVENTION

It is known that the symptoms of cardiac failure are related to some combination of circulatory volume expansion and reduced cardiac output. Therapy for cardiac failure has commonly involved the administration of an inotropic drug to increase the contractile force of the heart and the administration of a diuretic to increase urinary excretion of salt and water and to reduce left ventricular end diastolic pressure. Inotropic therapy with digitalis theoretically allows a greater stroke output for any given ventricular filling pressure. Objective evidence indicates digitalis may be of limited value in relieving symptoms associated with congestive heart failure. A diuretic may relieve the symptoms of volume expansion, but does not improve left ventricular performance. In the setting of mild congestive heart failure related to chronic coronary-artery disease or to non-ischemic forms of primary myocardial disease, digitalis and diuretic therapy is often effective in relieving digitalis and diuretic therapy is often effective in relieving symptoms of failure and in restoring a nearly normal functional state. However, in more severe degrees of failure, and in a setting of acute cardiac events when low cardiac output predominates, the conventional treatment may be inadequate in interrupting the physiological responses to the reduction in stroke volume. Physiological compensatory responses, while initially tending to restore normal tissue perfusion, also result in elevated peripheral vascular resistance. This elevated resistance to left ventricular outflow cannot be compensated for by the already dispersed left ventricle and cardiac output is even further depressed. Neither digitalis nor diuretics provide sufficient cardiotonic effect to adequately enhance cardiac output, and neither reduces the elevated peripheral vascular resistance.

Some vasodilator drugs which are known to relax the peripheral arteriolar bed have been found to be effective in relieving the signs of both elevated circulatory resistance and low cardiac output. A variety of vasodilator drugs have been employed to treat cardiac failure, both acutely administered intraveneous agents and chronically administered oral agents. The sites of action of these drugs vary so widely that each drug produces a rather distinct pattern of hemodynamic responses. The practical application of these drugs in the management of cardiac failure requires an understanding not only of circulatory effects of individual agents, but also of the physiological effects of various circulatory responses on cardiac and peripheral vascular function. Digitalis, a well known inotropic agent, has been shown to produce a disappointingly small improvement in pump function in a setting of acute myocardial infarctions.

Many vasodilator drugs, such as sodium nitroprusside, nitroglycerin, phentolamine and trimethaphan, have been demonstrated to improve pump functions in patients with left ventricular failure during the acute phase of myocardial infarction. The therapeutic aim of vasodilator drugs is to improve cardiac perfomance by reducing the elevated left ventricular filling pressure and by augmenting cardiac output. Arterial pessure may fall, but the desired hemodynamic effect can usually be achieved with little or no change in pressure. In some cases of severe congestive heart failure, reduction of outflow resistance leads to an increase in stroke volume with little or no change in heart rate. Under these circumstances, cardiac output may increase drastically and blood pressure does not change. In cases where blood pressure falls, an increase in reflex sympathetic nerve activity may cause side effects such as tachycardia, renin secretion and fluid retention which may limit the use of vasodilators.

SUMMARY OF THE INVENTION

In accordance with the present invention, a method of treating left ventricular heart failure by lowering the total peripheral resistance and increasing the cardiac output without any substantial change in blood pressure is provided which comprises administering to a warm blooded animal in need of such treatment an effective amount of an active phenyl-amidinourea compound of the structural Formula I.:

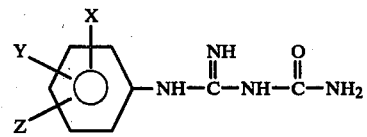

where:
X is hydrogen or halo;
Y is hydrogen, halo, haloloweralkyl, nitro loweralkyl or loweralkoxy;
Z is haloloweralkyl, haloloweralkoxy, hydroxy, loweralkysulfonyl, halo, loweralkoxy, loweralkyl, nitro or cyano;
and the non-toxic acid addition salts thereof.

Compounds of this invention which are preferred are described by general Formula I where:
X is hydrogen or halo;
Y is hydrogen, halo, loweralkyl or haloloweralkyl; and
Z is halo, loweralkyl, hydroxy, loweralkoxy or haloloweralkyl.

More particularly, the present invention relates to a method for treating left ventricular heart failure by dilating the arterial blood vessels without causing side effects commonly seen with vasodilators (i.e. tachycardia, renin secretion and fluid retention). The active compounds of the present invention may be used alone or in combination with diuretics and/or cardiac glycosides in the treatment of left ventricular failure.

The oral or parenteral administration of the active phenylamidinourea compounds of the present invention may be therapeutically useful, especially in the treatment of acute left ventricular failure, regurgitant ventricular lesions and chronic congestive heart failure on both an acute inpatient as well as outpatient basis.

DETAILED DESCRIPTION OF THE INVENTION

According to the method of the present invention, management of left ventricular heart failure is obtained by administering a concentration of about 20 mg to about 250 mg of a compound of general Formula I.

The compounds of Formula I may be prepared according to the process described in U.S. Pat. No. 4,088,785 of Diamond et al, which is incorporated herein by reference.

The compounds of Formula I have exhibited the ability to lower the total peripheral resistance and increase the cardiac output in normal animals. In patients with congestive heart failure, these responses would enable the heart to pump more blood and relieve the symptoms associated with poor ventricular performance.

Examples of phenylamidinourea compounds suitable for use in the method of the present invention include, among others:

o-chlorophenylamidinourea
m-chlorophenylamidinourea
p-chlorophenylamidinourea
(2,3-dichlorophenylamidino)urea
(2,4-dichlorophenylamidino)urea
(2,5-dichlorophenylamidino)urea
(2,6-dichlorophenylamidino)urea
(3,4-dichlorophenylamidino)urea
(3,5-dichlorophenylamidino)urea
(2,3,4-trichlorophenylamidino)urea
(2,3,5-trichlorophenylamidino)urea
(2,3,6-trichlorophenylamidino)urea
(2,4,5-trichlorophenylamidino)urea
(2,4,6-trichlorophenylamidino)urea
(3,4,5-trichlorophenylamidino)urea
(2,6-dibromophenylamidino)urea
(2-chloro-6-bromophenylamidino)urea
(4-chloro-3-bromophenylamidino)urea
(2-fluoro-6-chlorophenylamidino)urea
(2-iodo-6-chlorophenylamidino)urea
(2,4-dichloro-6-bromophenylamidino)urea
(2,6-dichloro-4-bromophenylamidino)urea
(2,4-dibromo-6-chlorophenylamidino)urea
(2,4-dichloro-6-bromophenylamidino)urea
(2,6-dichloro-4-bromophenylamidino)urea
(2-bromo-4-fluoro-6-chlorophenylamidino)urea
o-trifluoromethylphenylamidinourea
p-methylsulfonylphenylamidinourea
(2-chloro-4-cyanophenylamidino)urea
(2-methyl-4-trifluoromethylphenylamidino)urea
(2,6-dimethylphenylamidino)urea
(2,6-dimethyl-4-chlorophenylamidino)urea
(2,6-dimethyl-4-fluorophenylamidino)urea
(2,6-dichloro-3-hydroxyphenylamidino)urea
(2,6-dichloro-3-methoxyphenylamidino)urea
(2,6-dimethyl-4-nitrophenylamidino)urea
(2,6-dimethyl-4-trifluoromethylphenylamidino)urea
(2,6-dichloro-4-methylphenylamidino)urea
(2,4-dichloro-6-nitrophenylamidino)urea
(2,6-dichloro-4-nitrophenylamidino)urea
(2-trifluoromethyl-6-chlorophenylamidino)urea
(4-trifluoromethyl-2-fluorophenylamidino)urea
(2,4-dichloro-6-methylphenylamidino)urea
(2,6-dichloro-6-methylphenylamidino)urea
(2-methoxy-4-nitrophenylamidino)urea
(2,4-dichloro-6-methoxyphenylamidino)urea It is well known in the pharmacological arts that non-toxic acid addition salts of pharmacologically active amine compounds do not differ in activities from their free bases. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid |
| methane sulfonic acid, | nicotinic acid, |
| benzene sulfonic acid, | phthalic acid |
| acetic acid, | stearic acid, |
| propionic acid, | oleic acid |
| malic acid | abietic acid, etc. |

The compounds of Formula I can be administered orally or parenterally to various mammalian species in amounts ranging from about 20 to about 250 mg/kg/day divided into one or more doses for the pharmaceutical practice, for example, in the form of tablets, capsules, or an injectable solution.

Preferably, such compound is employed in combination with one or more adjuvants suited to the particular route of administration. Thus, in the case of oral administration, the compounds are modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such a composition can be formulated as tablets or enclosed in capsules for convenient administration. The compound also can be mixed with a liquifier and administered as an elixir, suspension, or the like. In the case of parenteral administration, the compound is conveniently formulated in saline to constitute an injectable solution. Other adjuvants and modes of administration are known to those skilled in the art.

Suitable pharmaceutical carriers are described in E. W. Martin et al., "Remington's Pharmaceutical Sciences", 14th Ed., Mark Publishing Company, Easton, Pa., 1965.

The following are detailed Examples which show pharmaceutical compositions containing the active compounds of Formula I and serve to illustrate the preparation thereof:

EXAMPLE I 25 g of (2,6-dichlorophenylamidino)urea
175 g of peanut oil
are intimately mixed with each other.
Portions of 200 mg. each of said mixture are filled into soft gelatin capsule thus containing 25 mg of the active phenylamidinourea compound.

EXAMPLE II

Ten thousand tablets for oral use, each containing 50 mg of (3-hydroxyphenylamidino)urea are prepared from the following types and amounts of material:

| Ingredient | Grams |
|---|---|
| (3-hydroxyphenylamidino)urea | 500 |
| Lactose U.S.P. | 350 |
| Potato Starch U.S.P. | 346 |

The mixture is moistened with an alcoholic solution of 20 grams of stearic acid and granulated through a sieve. After drying, the following ingredients are added:

| Ingredient | Grams |
|---|---|
| Potato Starch U.S.P. | 320 |
| Talcum | 400 |
| Magnesium Stearate | 500 |
| Lactose | 64 |

The mixture is thoroughly mixed and compressed into tablets.

EXAMPLE III

An elixir in which each 5 ml contains 50 mg of o-chlorophenylamidinourea is prepared by diluting 750 ml of invert sugar with 100 ml of water and adding to this 0.3 g of benzoic acid and 10 g of o-chlorophenylamidinourea. 100 ml of alcohol (U.S.P. containing 0.2 g of flavors) is added and water is added to a total volume of 1 liter. The solution is thoroughly mixed, filtered and bottled.

EXAMPLE IV

Capsules are prepared as follows:
150 g of m-chlorophenylamidinourea
3 g magnesium stearate,
2 g of finely divided silica sold under the trademark CAB-O-SIL by Godfrey L. Cabot, Inc., Boston, Mass., and
234 g of lactose.

The ingredients are thoroughly mixed with each other and the mixture is filled in gelatin capsules. Each capsule contains 500 mg of the composition and thus 150 mg of m-chlorophenylamidinourea.

EXAMPLE V

Tablets are prepared as follows:
100 g of (2,3-dichlorophenylamidino)urea
20 g of corn starch,
14 g of calcium carbonate, and
1 g of magnesium stearate.

The active compound and starch are thoroughly mixed, moistened with a 10 percent gelatin solution, and granulated by pressing through a No. 20 sieve. The granules are dried, thoroughly mixed with calcium carbonate and magnesium stearate, and compressed into tablets, each weighing about 125 mg and containing 100 mg.

EXAMPLE VI

Composition:
75 g of (2,6-dichlorophenylamidino)urea hydrochloride
50 g of microcrystalline cellulose,
10 g of polyvinylpyrrolidine,
5 g of magnesium stearate, and
85 g of starch.

The active compound and cellulose are intimately mixed, moistened with a polyvinylpyrrolidine solution in water, and granulated by pressing through a No. 10 sieve. The dried granules are mixed with starch and magnesium stearate and are compressed to dragee cores, each weighing 225 mg. The cores are now provided with an elastic subcoat of an aqueous sugar solution containing 60 g of powdered acacia, 60 g of powdered gelatin, and 600 g of sugar per liter of solution. Thereafter a dusting powder mixture of 180 g of powdered sugar, 60 g of powdered starch, 1 g of powdered talc, and 1 g of powdered acacia is applied to the dragee cores. Coating with the gelatin subcoat and dusting are repeated about five times. The thus treated cores are sugar coated in the coating pan with a 60 percent sugar solution. Sugar coating is repeated until each dragee weighs about 400 mg.

I claim:

1. A method for the treatment of left ventricular heart failure in a patient wherein low cardiac output predominates, which comprises administering to said patient in need of treatment, in an amount effective to lower the peripheral resistance and to increase the cardiac output without any substantial change in blood pressure, of at least one compound of the formula:

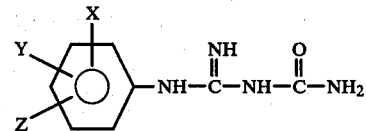

where:
X is hydrogen or halo;
Y is hydrogen, halo, haloloweralkyl, nitro loweralkyl or loweralkoxy;
Z is haloloweralkyl, haloloweralkoxy, hydroxy, loweralkylsulfonyl, halo, loweralkoxy, loweralkyl, nitro or cyano;
and the non-toxic acid addition salts thereof in a suitable pharmaceutically acceptable carrier.

2. A method according to claim 1 where:
X is hydrogen, chloro, bromo, fluoro, hydroxy or methoxy;
Y is hydrogen, chloro, methyl or trifluoromethyl;
Z is chloro, bromo, fluoro, methyl or trifluoromethyl.

3. A method according to claim 1 where the compound is selected from the group consisting of:
o-chlorophenylamidinourea,
m-chlorophenylamidinourea,
p-chlorophenylamidinourea,
(2,3-dichlorophenylamidino)urea,
(2,4-dichlorophenylamidino)urea,
(2,5-dichlorophenylamidino)urea,
(2,6-dichlorophenylamidino)urea,
(3,4-dichlorophenylamidino)urea, and
(3,5-dichlorophenylamidino)urea.

4. A method according to claim 3 where the compound is (2,6-dichlorophenylamidino)urea.

5. A method according to claim 1, where the compound is (2,6-dichloro-3-hydroxyphenylamidino)urea.

6. A method according to claim 1 where the compound is (2,6-dichloro-3-methoxyphenylamidino)urea.

* * * * *